(12) United States Patent
Noguchi et al.

(10) Patent No.: US 6,981,943 B2
(45) Date of Patent: Jan. 3, 2006

(54) RESPIRATION LEADING SYSTEM

(75) Inventors: Hiroki Noguchi, Burlington, MA (US); Manabu Inoue, Misato (JP); Wataru Iwai, Nagareyama (JP); Hiromitsu Kobayashi, Ishikawa (JP); Katsushige Amano, Kyoto (JP); Tadashi Yano, Kyoto (JP); Yoshinori Tanabe, Hirakata (JP)

(73) Assignees: Matsushita Electric Works, Ltd., Kadoma (JP); Matsushita Electric Industrial Co., Ltd., Kadoma (JP)

( * ) Notice: Subject to any disclaimer, the term of this patent is extended or adjusted under 35 U.S.C. 154(b) by 49 days.

(21) Appl. No.: 10/288,423

(22) Filed: Nov. 6, 2002

(65) Prior Publication Data

US 2003/0171643 A1    Sep. 11, 2003

(51) Int. Cl.
*A61M 21/00* (2006.01)

(52) U.S. Cl. .................................................. 600/26
(58) Field of Classification Search ............ 600/26–28; 601/41; 108/897, 198
See application file for complete search history.

(56) References Cited

U.S. PATENT DOCUMENTS

| 3,722,501 | A | * | 3/1973 | Derouineau | 600/27 |
| 3,991,304 | A | * | 11/1976 | Hillsman | 600/538 |
| 4,573,449 | A | * | 3/1986 | Warnke | 600/28 |
| 4,665,926 | A | * | 5/1987 | Leuner et al. | 600/529 |
| 5,395,301 | A | * | 3/1995 | Russek | 601/41 |

FOREIGN PATENT DOCUMENTS

| JP | 3-222964 | 10/1991 |
| JP | 2000-357591 | 12/2000 |

* cited by examiner

*Primary Examiner*—Samuel G. Gilbert
(74) *Attorney, Agent, or Firm*—Oblon, Spivak, McClelland, Maier & Neustadt, P.C.

(57) ABSTRACT

Disclosed is a respiration leading system which can leads a living body to respire so that relaxation is effectively induced without any physiological load even if a respiration exercise feedback is not employed. This system comprises a control unit and a sense-stimulating unit. The control unit makes the sense-stimulating unit change the output energy for stimulating a sense of the living body so that the living body is induced to inhale and exhale as a physiological reaction. The energy change is done within the range of a respiration period x(sec) and a parameter y defined as 2 sec<x<12 sec and 0.85<y<1.45 (a region x≦4 sec and y≧1.3 is excluded). The parameter y is a ratio of exhaling time to inhaling time. The energy output in the first half period corresponding to either inhaling or exhaling and the energy output in the latter half corresponding to the other, induce the living body to respire.

20 Claims, 8 Drawing Sheets

RESPIRATION LEADING SYSTEM

BACKGROUND OF THE INVENTION

The present invention relates to a respiration leading system for inducing relaxation effectively by using a sense-stimulating unit.

Many kinds of stress are prevailing in our society today, and people are under the continuous psychological and physiological stresses. A respiration of a person who is under psychologically over-stressed becomes shallow and rapid unconsciously. Such a respiration also causes physiological strain like a rapid heartbeat or a rise of blood pressure through the autonomic nervous system.

Conventionally, there have been such an apparatus or a method available that lead a person (user or living body) to respire by repeated on-and-off illumination of light or by changing the intensity of light and color tone so that he (or she) can escape from the stress (see Japanese Unexamined Patent Publication No. HEI03-222964 and No. 2000-357591).

A setting of a respiration period must be most carefully done in the respiration leading for the relaxation. If the period is too short, the above-mentioned stress is caused, and if too long, the respiration is not continued and also an excessive load arises and significantly affects the circulatory system. To avoid those problems, a method or system was developed which elongates the respiration period from the short period at the respiration leading start to the longer period with which respiration is done without any difficulty, by using a feedback from the respiratory movement through some sort of method. However, such a system is too complex and expensive.

If a range of respiration period which is effective for relaxation is made clear, the feedback is not necessary for the system and it is possible to realize a simple and low cost respiration leading system.

A time balance between inhaling and exhaling is a important parameter of respiration for relaxation as well as the period of the respiration.

During the exhaling cycle the parasympathetic nervous system of the autonomic nervous system is activated to release a body from tension, and conversely during the inhaling cycle the sympathetic nervous system is activated to make the body keep tension.

Therefore, it is important to set the exhaling time longer than the inhaling time so that the relaxation will be induced by respiration control. The ratio of the exhaling time to inhaling time (hereafter called as exhaling-ratio) in the spontaneous respiration is known to vary with the respiration period, for example during sleeping the respiration period becomes longer and the exhaling-ratio becomes larger.

It must be avoided to temporarily stop respiration during the respiration leading for the relaxation. Such a respiration-stopped state causes an excessive load for the circulatory system.

If respiration leading is done with an unnatural respiration pattern such as largely different from spontaneous respiration, a person under the leading will stop the respiration because of uneasiness to match the respiration to the pattern. Therefore, it is effective for relaxation to use natural respiration pattern in which the exhaling-ratio is changed according to the change of the respiration period in the process to elongate the respiration period. Here, the relaxation means a relaxed state including a sleeping state as the result of deep relaxation.

SUMMARY OF THE INVENTION

In view of the above, it is an object of the present invention to provide a respiration leading system that can lead a living body to respire so that relaxation is effectively induced without any physiological load even if a respiration exercise feedback is not employed.

According to an aspect of the present invention, a respiration leading system having a control unit and a sense-stimulating unit for outputting energy periodically for stimulating a sense of a living body so that the living body is induced to inhale and exhale as a physiological reaction.

The control unit makes the sense-stimulating unit change the output energy with a period x second and a parameter y.

The period x corresponds to respiration period and the parameter y is a ratio of exhaling time to inhaling time. The x and y are defined in a range, $2 \text{ sec} < x < 12 \text{ sec}$ and $0.85 < y < 1.45$ (a region $x \leq 4$ sec and $y \geq 1.3$ is excluded).

The energy output in the first part of the period corresponding to either inhaling or exhaling and the energy output in the rest of the period corresponding to the other, induce the living body to respire.

To achieve above-mentioned object, a variation of a respiration period and a ratio of exhaling time to inhaling time (exhaling-ratio) based on results of psychological (subjective) and physiological experiments are used in the respiration leading system.

Preliminary experiments were done to determine the respiration period and the exhaling-ratio. The respiration periods x of 6-levels i.e. 2 sec, 4 sec, 6 sec, 8 sec, 10 sec, and 12 sec, and exhaling-ratios y of 5-levels i.e. 0.85, 1.00, 1.15, 1.30, and 1.45 were combined and total of 30 cases were examined to search combinations in which respiration can be done. The experiments revealed that respiration can be sustained in a region $2 \text{ sec} < x < 12 \text{ sec}$ and $0.85 < y < 1.45$ ($x \leq 4$ sec and $y \geq 1.3$ is excluded), shown in FIG. 1, but outside of this region respiration can not last.

Consequently, the respiration leading for the relaxation can be realized without any physiological load by performing in the above-mentioned region without any feedback from respiration exercise.

The relaxation becomes effective in this region, because it is not necessary to intentionally stop the respiration in order to synchronize the respiration with unfamiliar leading signals.

According to a further aspect of the present invention, the parameter y is increased or decreased in accordance with said period x is increased or decreased.

Consequently, a further technical advantage is achieved that the relaxation effect is further promoted.

According to a further aspect of the present invention, sense-stimulating unit emits light energy for leading a living body to respire and a respiration pattern is indicated by change of light intensity and/or color tone.

Consequently, a further technical advantage is achieved that light can be recognized through eyelids, so there is the same effect even if eyes are closed.

According to a further aspect of the present invention, the sense-stimulating unit outputs one or plural kinds of energy in a state of light, sound, wind, heat, and pressure.

Consequently, a further technical advantage is achieved that energies in those states can stimulate senses of a living body, and can induce it to inhale and exhale as a physiological reaction. Thus the relaxation becomes further effective by multiple uses of those energies.

According to an aspect of the present invention, a respiration leading system having a control unit and a sense-stimulating unit for outputting energy periodically for stimulating a sense of a living body so that the living body is induced to inhale and exhale as a physiological reaction.

The control unit makes the sense-stimulating unit change the output energy with a function of period x(sec) and a parameter y.

The period x corresponds to respiration period and the parameter y is a ratio of exhaling time to inhaling time. The x and y are defined in a region, $1 \leq y < 1.15 + (x-6) \cdot 0.075$, for 6 sec $\leq$ x < 8 sec, and $1 < y \leq 1.3$, for 8 sec $\leq$ x < 10 sec.

The parameter y is increased or decreased in accordance with said period x is increased or decreased.

The energy output in the first part of the period corresponding to either inhaling or exhaling and the energy output in the rest of the period corresponding to the other, induce the living body to respire.

Consequently, the respiration leading for the relaxation can be realized under the most preferable conditions.

To get the most preferable conditions for respiration leading, preliminary experiments, like as mentioned above, were done within the range of respiration period x and exhaling-ratio y already determined above. Thus the respiration period x and the exhaling-ratio y of the most preferable conditions were determined based on results of psychological (subjective) and physiological experiments.

The period of spontaneous respiration of a human being is said to be about 3 to 5 sec. It is necessary to elongate the respiration period than the period of spontaneous respiration to achieve the respiration leading for relaxation.

Then the respiration periods x of 4-levels i.e. 6 sec, 8 sec, 10 sec, 12 sec, and the exhaling-ratios y of 3-levels i.e. 1.00, 1.15, 1.30 were combined and total of 12 cases were examined. The respiration conditions were controlled to be in the 12 cases and (1) easiness of respiration and (2) relaxation levels were evaluated. The results were shown in the FIG. 2 and FIG. 3.

(1) About easiness of respiration, as shown in FIG. 2, at period x=6 sec the evaluation is best and at x=10 sec worst. About the relation to the exhaling-ratio, at x=6 sec and the exhaling-ratio y=1.00 the evaluation is best but its evaluation drops with the increase of x, and at x=8 to 10 sec the evaluation for y=1.15 becomes best. Thus if the easiness of respiration is considered, it is preferable for x=6 sec to set around y=1, and for x=8 to 10 sec around y=1.15.

(2) About relaxation levels, as shown in FIG. 3, the evaluation is high at x=6 sec and y=1, x=8 sec and y=1.15, x=10 sec and y=1.3.

The variation of the heartbeat at controlled condition from average heartbeat at spontaneous respiration is also examined and shown in FIG. 4. The decrease of the heartbeat is most remarkable at x=8 sec and y=1.3. This means that the physiological tension is supposed to be smallest at this respiration condition.

It is clarified through the psychological (subjective) evaluation on respiration conditions, that respiration is easy and relaxation level is good under the condition in the range from the respiration period x=6 sec and exhaling-ratio y=1 to x=8 sec and y=1.15.

The heartbeat data suggest that the respiration at x=8 sec and y=1.3 may reduce the physiological tension.

As the summary, the method to increase x and y from x=6 sec and y=1 to x=8 sec and y=1.15 to 1.3 gradually is considered to be best for respiration leading for relaxation.

The best region of the condition for respiration leading with the aim of relaxation is, as shown in FIG. 5, defined by the equations;

$1 \leq y < 1.15 + (x-6) \cdot 0.075$, for 6 sec $\leq$ x < 8 sec, and $1 < y \leq 1.3$, for 8 sec $\leq$ x < 10 sec.

For respiration leading with the aim of relaxation, a function that connects any two points in this region can be successfully used to lead respiration by gradually increasing the respiration period x and exhaling-ratio y.

The exhaling time is never shorter than inhaling time in the spontaneous respiration. Thus if respiration leading is done below x=6 sec, it is preferable to set exhaling-ratio y=1. Because a sensitivity of a human being contains about 10 percent error, above-mentioned respiration period and exhaling-ratio also contain about 10 percent error.

Other features and advantages of the present invention will be apparent from the following description taken in conjunction with the accompanying drawings, in which like reference characters designate the same or similar parts throughout the figures thereof.

The present disclosure relates to subject matter contained in priority Japanese Patent Application No. 2001-70061 and No. 2002-63240, the contents of which is herein expressly incorporated by reference in its entirety.

DESCRIPTION OF THE PREFERRED EMBODIMENTS (First Embodiment)

Figure 1:
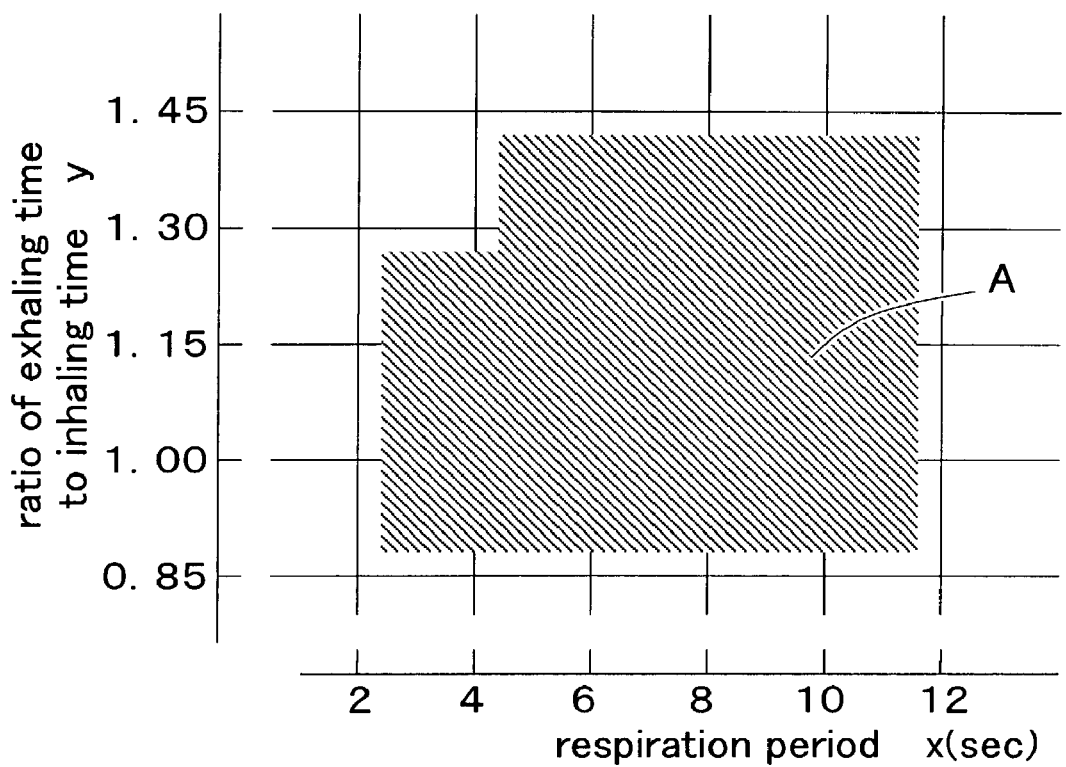
FIG. 1 is a graph for showing the range of the ratio of exhaling time to inhaling time and the range of the respiration period in accordance with the present invention.
Figure 2:
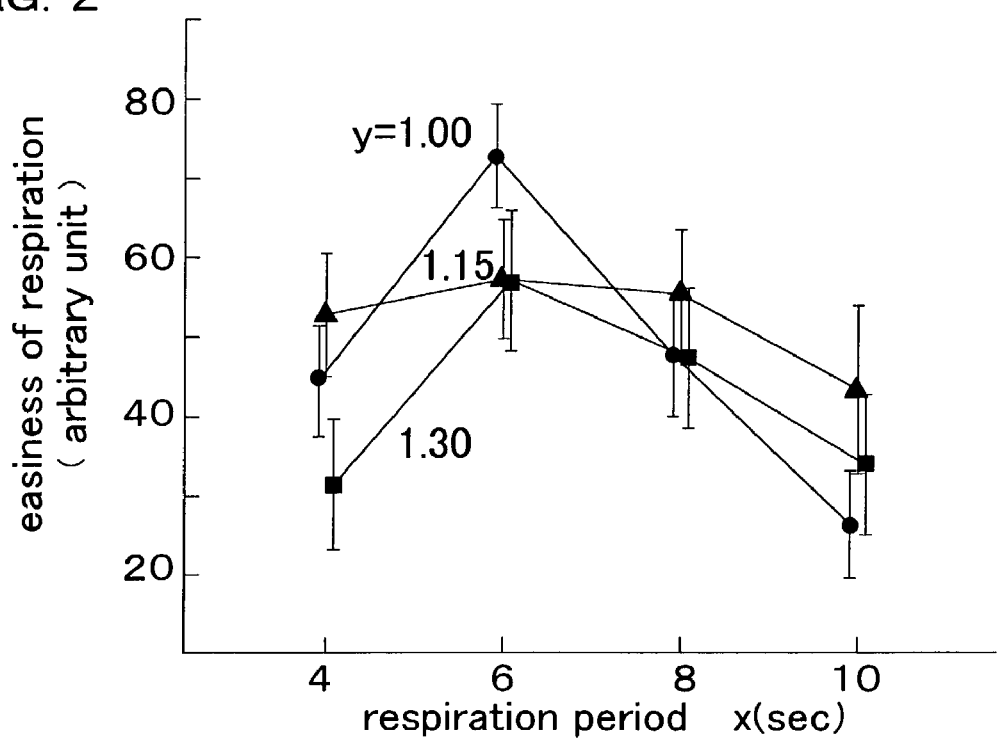
FIG. 2 is a graph for showing a relation between the easiness of respiration and the respiration period for three levels of exhaling-ratio y.
Figure 3:
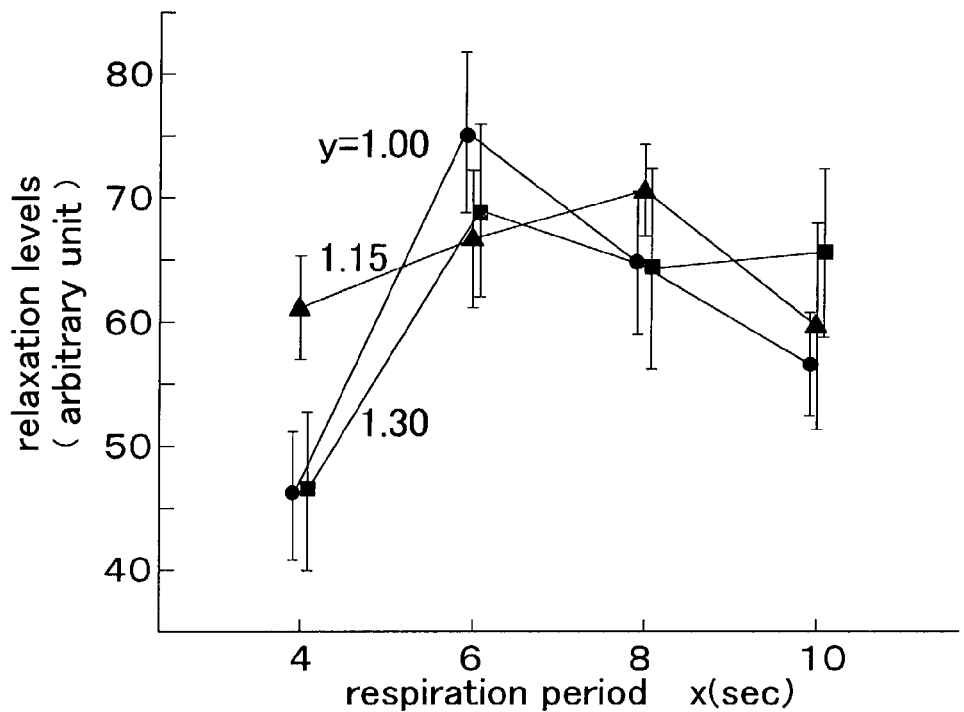
FIG. 3 is a graph for showing a relation between the relaxation levels and the respiration period for three levels of exhaling-ratio y.
Figure 4:
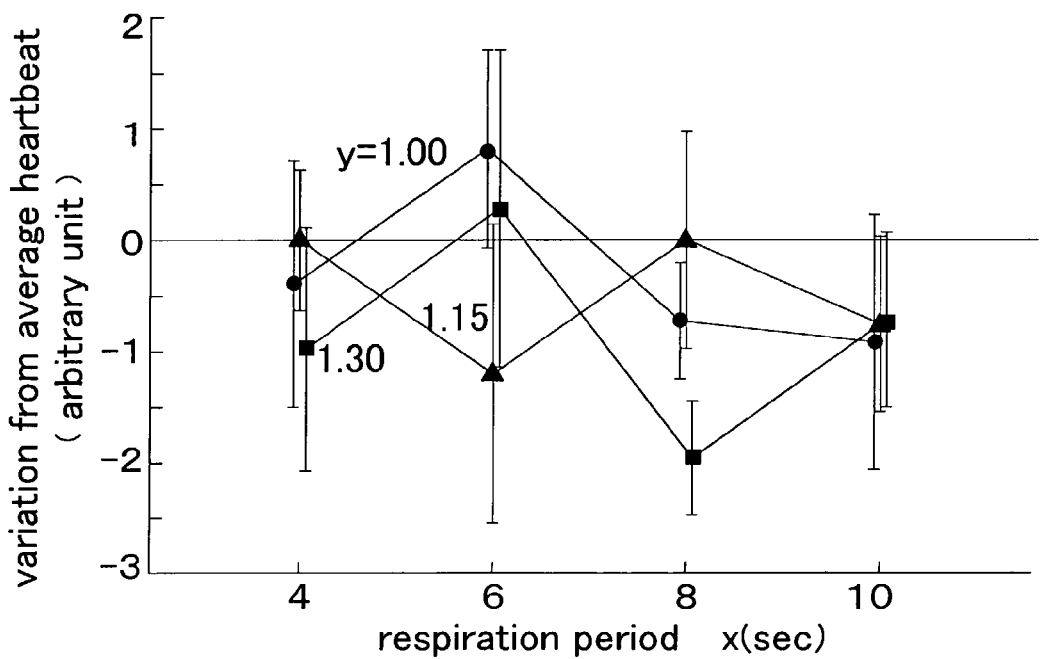
FIG. 4 is a graph for showing a relation between the variation from the average heartbeat and the respiration period for three levels of exhaling-ratio y.
Figure 5:
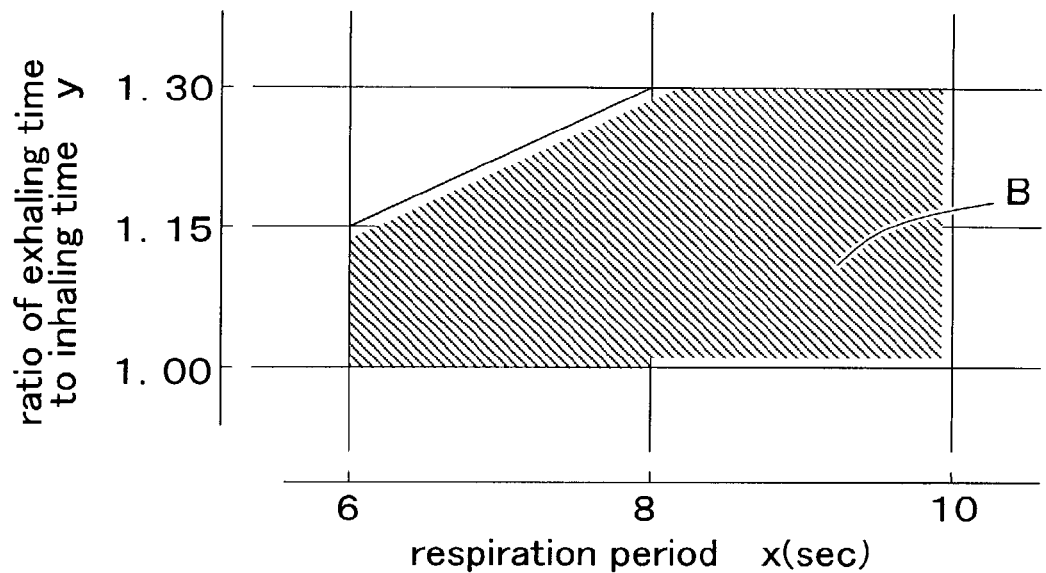
FIG. 5 is a graph for showing the range of the ratio of exhaling time to inhaling time and the range of the respiration period in accordance with the present invention.
Figure 6:
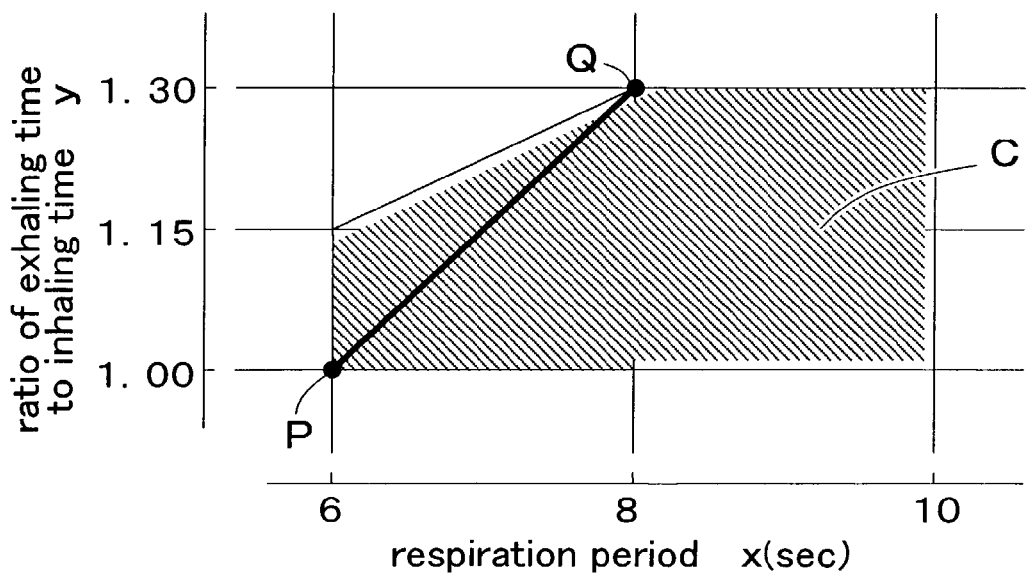
FIG. 6 is a graph for showing the range of the ratio of exhaling time to inhaling time and the range of the respiration period in accordance with a first embodiment of the present invention.

A first embodiment is described referring to FIG. 6. A line connecting point P and Q in the figure is used as a function for respiration leading. A period of the spontaneous respiration has some individual differences of about 3 to 5 sec. Thus the period at the start of respiration leading is set below 6 sec, and the system is made to be able to adjust the respiration period to the user's usual respiration period. The period is gradually elongated from the start period up to 6 sec with exhaling-ratio y=1 kept. From the point P of respiration period x=6 sec and exhaling-ratio y=1 up to point Q of x=8 sec and y=1.3, the exhaling-ratio is increased gradually linked to the increase of the respiration period.

(Second Embodiment)

Figure 7:
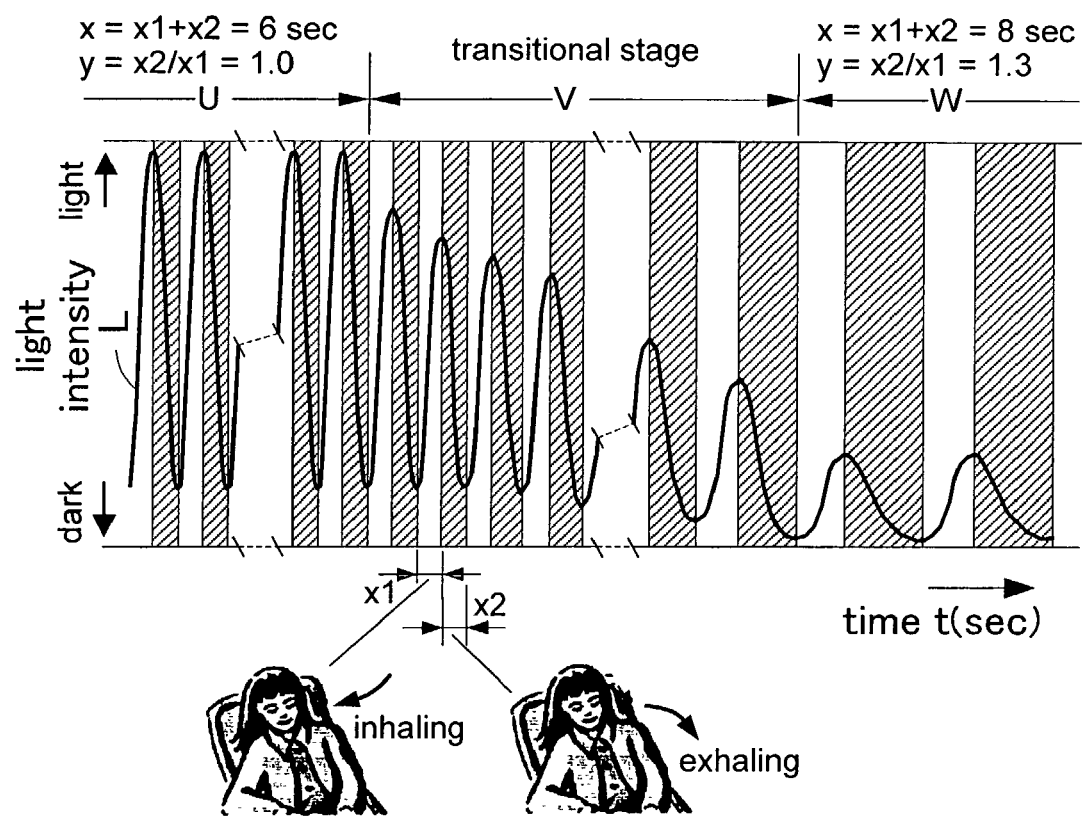
FIG. 7 is a graph for showing the light intensity change with time in accordance with a second embodiment of the present invention.
Figure 8:
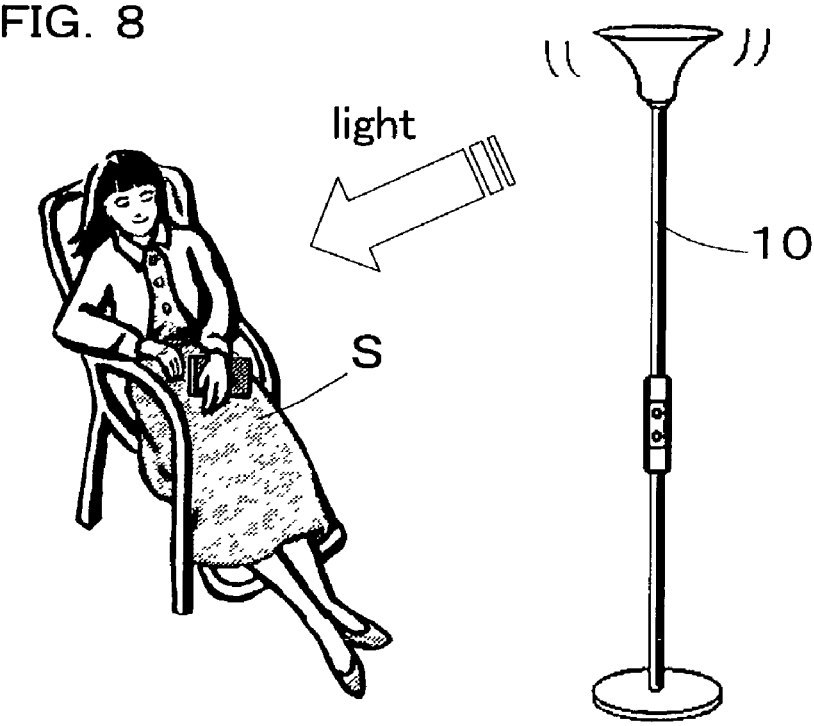
FIG. 8 is a schematic drawing for showing the respiration leading with light in accordance with a second embodiment of the present invention.
Figure 9:
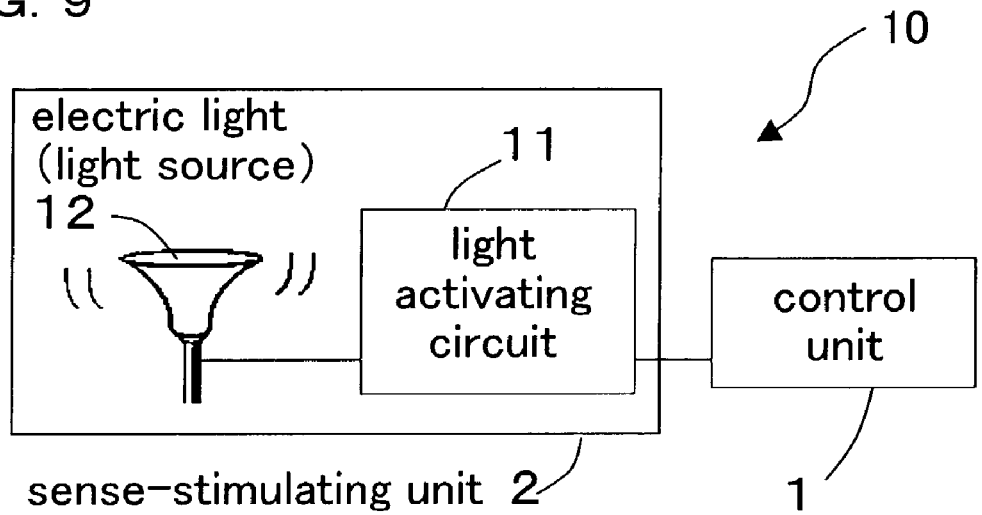
FIG. 9 is a block diagram for showing a configuration of the respiration leading system in accordance with a second embodiment of the present invention.

A respiration leading by lighting is described referring to FIG. 7 to FIG. 9. For the respiration leading with the aim of relaxation, it is important to lead a person to respire smoothly to avoid temporally stopping of respiration. Thus it is preferable not only to show the timing of respiration but also to show information continuously about inhaling and exhaling action. Thus if the inhaling action is presented by increase of light intensity and exhaling action is presented by decrease of light intensity the user can synchronize respiration with a leading pattern or a light intensity pattern.

Since during the exhaling cycle the parasympathetic nervous system of the autonomic nervous system is activated to release a body from tension, it is reasonable that the lighting pattern is related with intensity increase to inhaling and with intensity decrease to exhaling.

One concrete example of the lighting pattern is shown in FIG. 7. The light intensity L is made of smooth curves like sinusoidal wave. The hatched regions in the figure show the exhaling cycle (time x2) and the light intensity is decreased, and the blank regions show the inhaling cycle (time x1) and the light intensity is increased. The respiration leading process is divided into three stages; stage U, V, and W. At stage U, introductory stage, the respiration period is set as x=6 sec and the exhaling-ratio is set as y=1. The stage V is a main stage, and the period x and exhaling-ratio y are gradually increased, but the average light intensity is decreased gradually, i.e. transitional stage. At stage W, final stage, the period and exhaling-ratio are set constant as x=8 sec and y=1.3, and the user is assumed to be in deep relaxation or in sleeping. In the final stage, the light intensity is set most low or turned off by fade-out. After relaxation time, the user will wake up, so the light intensity is increased and also the period and exhaling-ratio are increased to help awakening and smooth continuation to the daily activity.

The respiration leading pattern can be configured by color tone instead of light intensity or combined with light intensity. For the exhaling cycle, blue color is preferable which shows good effect for relaxation. The respiration leading by lighting also can work for the user who is closing the eyelids.

A schematic drawing for showing the respiration leading with light is given in FIG. 8, and a block diagram of the configuration of the respiration leading system is shown in FIG. 9.

The user S feels the lighting pattern from the respiration leading system 10 which has a control unit 1 and sense-stimulating unit 2. The sense-stimulating unit 2 has light activating circuit 11 and electric light (light source) 12. The control unit 1 controls the sense-stimulating unit 2, and makes it output energy of light as a respiration leading signal pattern. The light activating circuit has circuits for light-turn-on/off and a color tone tuner.

Several kinds of forms of light source 12 can be used, for example, a ceiling light, a pendant light, a bracket light, a floor stand light, a desk stand light, etc.

Those of goggle, eyeglass, or eye-mask (see Japanese Patent Application No. 2001-349582) type light sources are also applicable. Such a light source can irradiate localized light onto the user's eyes and it can be made compact and wearable for portable use. It can be used during a trip or used without any influences on another person.

The light source 12 itself is, for example, an incandescent lamp. Another light source such as an LED (light emitting diode), an EL (Electro-luminescence), an HID (high-intensity discharge lamp), a fluorescent lamp, or the like can be used.

(Third Embodiment)

Figure 10:
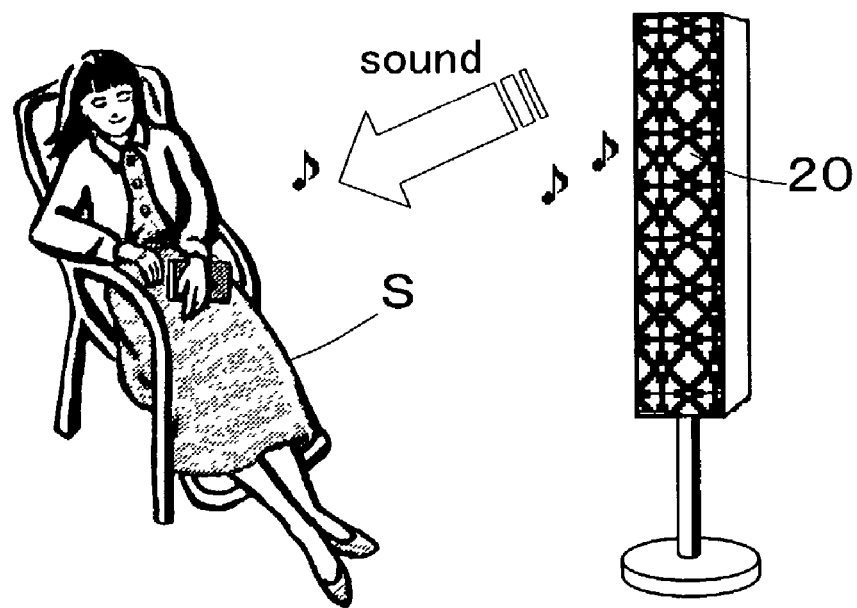
FIG. 10 is a schematic drawing for showing the respiration leading with sound in accordance with a third embodiment of the present invention.
Figure 11:
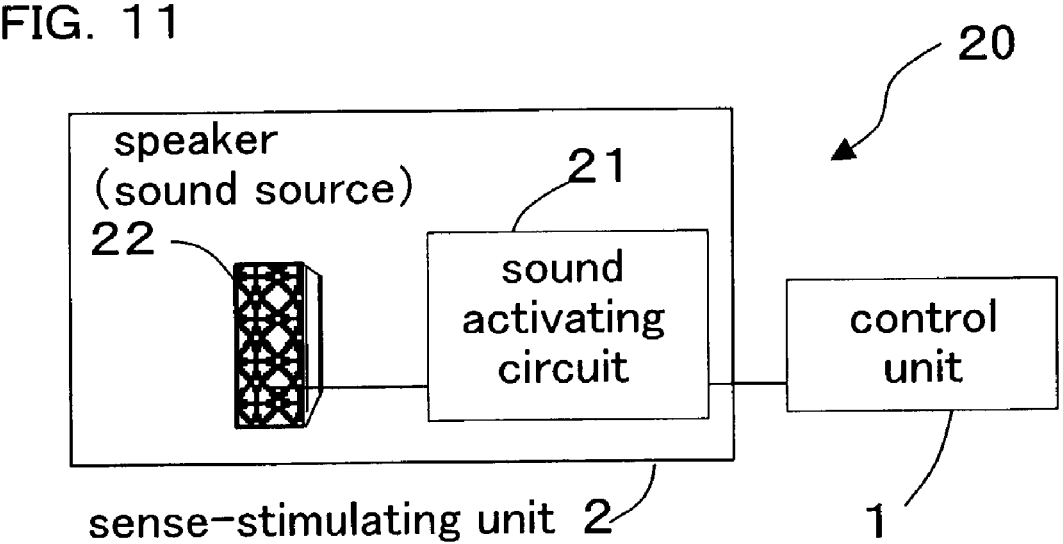
FIG. 11 is a block diagram for showing a configuration of the respiration leading system in accordance with a third embodiment of the present invention.

A schematic drawing for showing the respiration leading with sound is given in FIG. 10, and a block diagram of the configuration of the respiration leading system is shown in FIG. 11.

The user S hears the sound pattern from the respiration leading system 20 which has a control unit 1 and sense-stimulating unit 2. The sense-stimulating unit 2 has sound activating circuit (including amplifier) 21 and speaker (sound source) 22. The control unit 1 controls the sense-stimulating unit 2, and makes it output energy of sound as a respiration leading signal pattern.

The sound volume is increased in the inhaling cycle and decreased in the exhaling cycle so that the user's respiration exercise is continuously expressed and guided by the volume change. As to the kind of sound, natural sound like ripple is better for relaxation effect.

(Fourth Embodiment)

Figure 12:
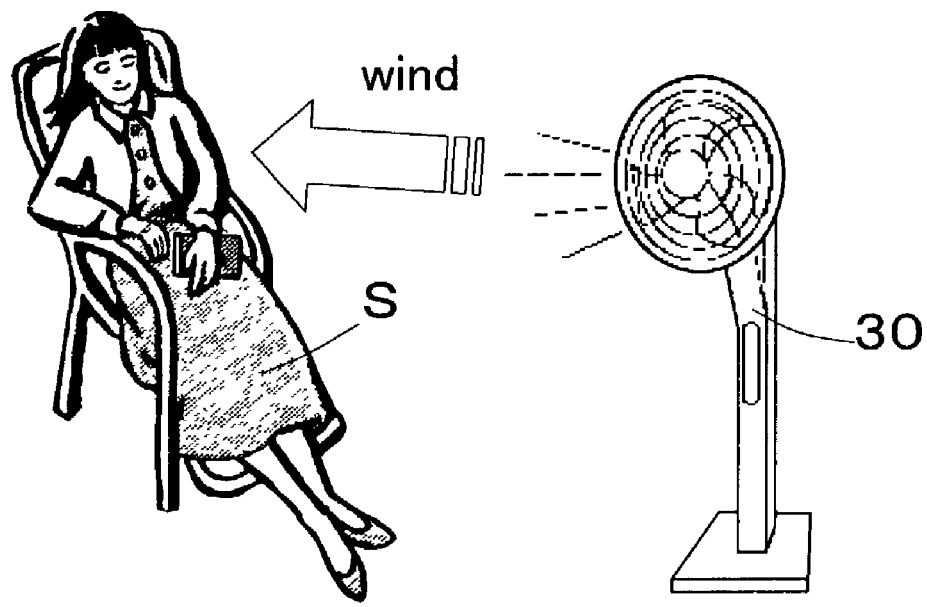
FIG. 12 is a schematic drawing for showing the respiration leading with wind in accordance with a fourth embodiment of the present invention.
Figure 13:
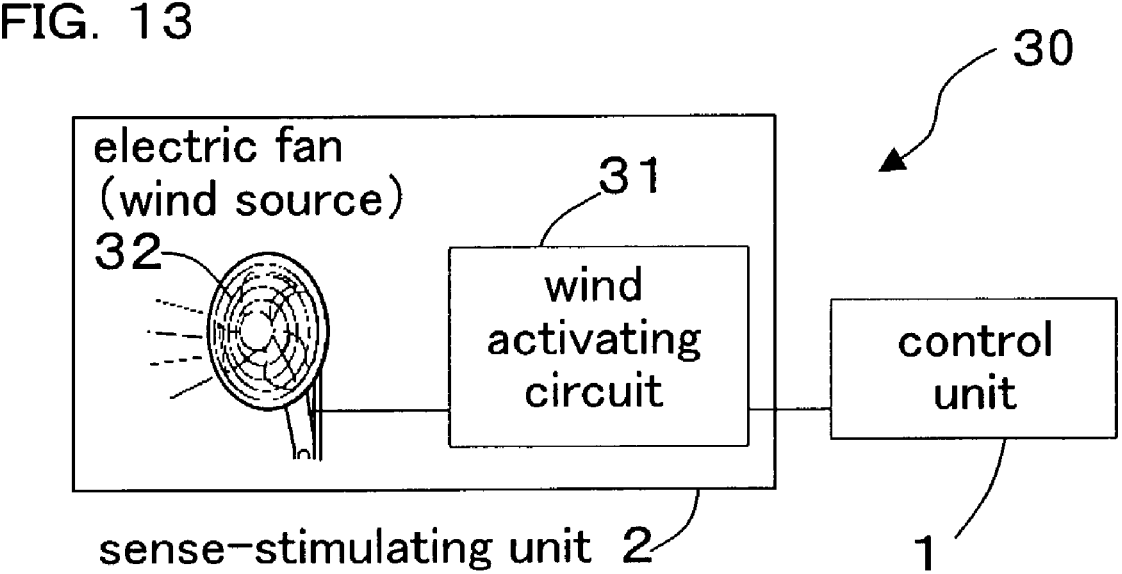
FIG. 13 is a block diagram for showing a configuration of the respiration leading system in accordance with a fourth embodiment of the present invention.

A schematic drawing for showing the respiration leading with wind is given in FIG. 12, and a block diagram of the configuration of the respiration leading system is shown in FIG. 13.

The user S feels the wind pattern from the respiration leading system 30 which has a control unit 1 and sense-stimulating unit 2. The sense-stimulating unit 2 has wind activating circuit 31 and electric fan (wind source) 32. The control unit 1 controls the sense-stimulating unit 2, and makes it output energy of wind as a respiration leading signal pattern.

The wind intensity is increased in the inhaling cycle and decreased in the exhaling cycle so that the user's respiration exercise is continuously expressed and guided by the airflow change.

(Fifth Embodiment)

Figure 14:
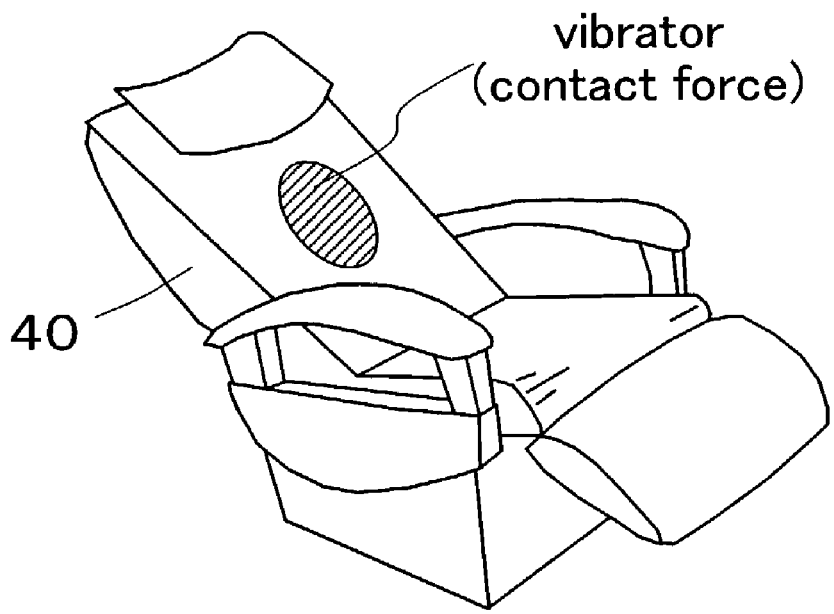
FIG. 14 is a schematic drawing for showing the respiration leading with contact pressure in accordance with a fifth embodiment of the present invention.
Figure 15:
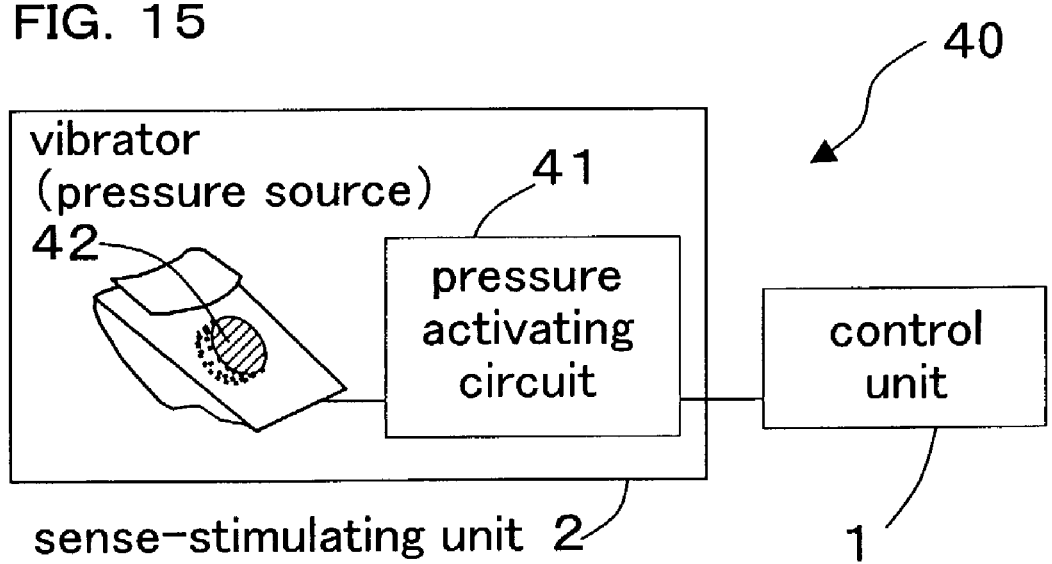
FIG. 15 is a block diagram for showing a configuration of the respiration leading system in accordance with a fifth embodiment of the present invention.

A schematic drawing for showing the respiration leading with contact pressure is given in FIG. 14, and a block diagram of the configuration of the respiration leading system is shown in FIG. 15.

A user on the chair feels the contact pressure pattern on the back from the respiration leading system 40 which has a control unit 1 and sense-stimulating unit 2. The sense-stimulating unit 2 has pressure activating circuit 41 and vibrator (pressure source) 42. The control unit 1 controls the sense-stimulating unit 2, and makes it output energy of pressure as a respiration leading signal pattern.

The pressure intensity (amplitude of the vibration and/or frequency) is increased in the inhaling cycle and decreased in the exhaling cycle so that the user's respiration exercise is continuously expressed and guided by the vibration change.

(Sixth Embodiment)

Any combination of the energy in the state of light, sound, wind, heat, and pressure can be used to lead a person to respire. For example, light and sound combination, or light, sound, and contact pressure combination are effectively used.

The present invention can be implemented in various forms without being limited by the configuration of the embodiment described above.

What is claimed is:

1. A respiration leading system comprising:
   a sense-stimulating device configured to stimulate a physiological sense of a living body by outputting stimuli each having a respiration period component, an inhaling time component and an exhaling time component so as to induce inhale and exhale as a physiological reaction; and
   a control device configured to control the stimuli by changing the respiration period component, x, and a ratio of the exhaling and inhaling time components, y, wherein 2 sec<x<12 sec and 0.85<y<1.45 excluding a value satisfying x≦4 sec and y≧1.3 and said control device is configured to increase y as x is increased or decrease y as x is decreased.

2. The system set forth in claim 1, wherein said sense-stimulating device is configured to emit light as the stimuli for leading a living body to respire and said control device is configured to change at least one of intensity and color tone of the light.

3. The system set forth in claim 1, wherein said sense-stimulating device is configured to output at least one of light, sound, wind, heat, and pressure as the stimuli.

4. The system set forth in claim 1, wherein said control device is configured to reduce intensity of the stimuli as the respiration period component becomes longer.

5. The system set forth in claim 1, wherein said control device is configured to provide an introduction stage, a transition stage and a relaxation stage in controlling said sense-stimulating device, the introduction stage having a larger value of the respiration period component than the relaxation stage, and the transition stage being a transition period from the introduction stage to the relaxation stage.

6. The system set forth in claim 5, wherein said control device is configured to provide 6 second of the respiration period component during the introduction stage and 8 second of the respiration period component during the relaxation stage.

7. An respiration leading system comprising:
   a sense-stimulating device configured to stimulate a physiological sense of a living body by outputting stimuli each having a respiration period component, an inhaling time component and an exhaling time component so as to induce inhale and exhale as a physiological reaction; and
   a control device configured to control the stimuli by changing the respiration period component, x, and a ratio of the exhaling and inhaling time components, y, wherein 1≦y<1.15+(x−6)·0.075, for 6 sec≦x<8 sec, and 1<y≦1.3, for 8 sec≦x<10 sec, and said control device is configured to increase y, as x is increased or said control device is configured to decrease y, as x is decreased.

8. The system set forth in claim 5, wherein said sense-stimulating device is configured to emit light as the stimuli for leading a living body to respire and said control device is configured to change at least one of intensity and color tone of the light.

9. The system set forth in claim 7, wherein said sense-stimulating device is configured to output at least one of light, sound, wind, heat, and pressure as the stimuli.

10. The system set forth in claim 7, wherein said control device is configured to reduce intensity of the stimuli as the respiration period component becomes longer.

11. The system set forth in claim 7, wherein said control device is configured to provide an introduction stage, a transition stage and a relaxation stage in controlling said sense-stimulating device, the introduction stage having a larger value of the respiration period component than the relaxation stage, and the transition stage being a transition period from the introduction stage to the relaxation stage.

12. The system set forth in claim 11, wherein said control device is configured to provide 6 second of the respiration period component during the introduction stage and 8 second of the respiration period component during the relaxation stage.

13. A respiration leading system comprising:
   sense-stimulating means for stimulating a physiological sense of a person by outputting stimuli each having a respiration period component, an inhaling time component and an exhaling time component so as to induce inhale and exhale as a physiological reaction; and
   a control device configured to control the stimuli by changing the respiration period component, x, and a ratio of the exhaling and inhaling time components, y, wherein 2 sec<x<12 sec and 0.85<y<1.45 excluding a value satisfying x≦4 sec and y≧1.3 and said control device is configured to increase y as x is increased or decrease y as x is decreased.

14. The system set forth in claim 13, wherein said sense-stimulating means emits light as the stimuli for leading a living body to respire and said control device is configured to change at least one of intensity and color tone of the light.

15. The system set forth in claim 13, wherein said sense-stimulating means outputs at least one of light, sound, wind, heat, and pressure as the stimuli.

16. The system set forth in claim 13, wherein said control device is configured to reduce intensity of the stimuli as the respiration period component becomes longer.

17. The system set forth in claim 13, wherein said control device is configured to provide an introduction stage, a transition stage and a relaxation stage in controlling said sense-stimulating means, the introduction stage having a larger value of the respiration period component than the relaxation stage, and the transition stage being a transition period from the introduction stage to the relaxation stage.

18. The system set forth in claim 17, wherein said control device is configured to provide 6 second of the respiration period component during the introduction stage and 8 second of the respiration period component during the relaxation stage.

19. The system set forth in claim 17, wherein said control device is configured to provide 6 second of the respiration period component and 1.0 of the ratio of the exhaling and inhaling time components during the introduction stage and 8 second of the respiration period component and 1.3 of the ratio of the exhaling and inhaling time components during the relaxation stage.

20. The respiration leading system set forth in claim 13, wherein $1 \leq y < 1.15 + (x-6) \cdot 0.075$, for $6 \text{ sec} \leq x < 8 \text{ sec}$, and $1 < y \leq 1.3$, for $8 \text{ sec} \leq x < 10 \text{ sec}$, and said control device is configured to increase y, as x is increased or said control device is configured to decrease y, as x is decreased.

* * * * *

UNITED STATES PATENT AND TRADEMARK OFFICE
CERTIFICATE OF CORRECTION

PATENT NO. : 6,981,943 B2
DATED : January 3, 2006
INVENTOR(S) : Noguchi et al.

It is certified that error appears in the above-identified patent and that said Letters Patent is hereby corrected as shown below:

<u>Title page,</u>
Item [30], Foreign Application Priority Data, should read:
-- [30]     Foreign Application Priority Data
    Mar. 08, 2002    (JP)..............................2002-063240 --.

Signed and Sealed this

Seventh Day of March, 2006

JON W. DUDAS
*Director of the United States Patent and Trademark Office*